United States Patent [19]

Middleton et al.

[11] Patent Number: 4,603,448
[45] Date of Patent: Aug. 5, 1986

[54] ROTARY ELECTRIC TOOTHBRUSH

[75] Inventors: Frederic H. Middleton; David V. Mollenhoff, both of Madison; Theodore L. Taylor, Manitowoc; Thomas N. Vaughn, Columbus, all of Wis.

[73] Assignee: MTV Associates, Madison, Wis.

[21] Appl. No.: 742,198

[22] Filed: Jun. 7, 1985

[51] Int. Cl.⁴ ............................................. A46B 13/02
[52] U.S. Cl. ...................................... 15/22 R; 15/23; 74/22 A
[58] Field of Search ......................... 15/22 R, 23, 24; 74/22 A

[56] References Cited

U.S. PATENT DOCUMENTS

| | | | |
|---|---|---|---|
| 2,124,245 | 7/1938 | Merkel | 15/23 |
| 2,279,982 | 4/1942 | Glynn | 15/23 |
| 2,858,701 | 11/1958 | Willcox | 15/23 X |
| 3,161,899 | 12/1964 | Poizat | 15/23 |
| 3,235,897 | 2/1966 | Fortenberry | 15/24 |
| 3,512,201 | 5/1970 | Taylor | 15/23 |
| 3,512,202 | 5/1970 | Taylor | 15/23 |
| 3,551,932 | 1/1971 | Grossman | 15/23 |
| 3,739,416 | 6/1973 | Kurachi | 15/23 |
| 3,800,350 | 4/1974 | Francolino | 15/23 |
| 3,829,922 | 8/1974 | Koblanski | 15/23 |
| 3,925,841 | 12/1975 | Caliendo | 15/23 |
| 4,163,300 | 8/1979 | Quint | 15/23 |
| 4,304,023 | 12/1981 | O'Rourke | 15/23 |
| 4,313,237 | 2/1982 | Smith | 15/23 |
| 4,397,055 | 8/1983 | Cuchiara | 15/23 X |

Primary Examiner—Edward L. Roberts
Attorney, Agent, or Firm—Isaksen, Lathrop, Esch, Hart & Clark

[57] ABSTRACT

A rotary electric toothbrush including a power handle having a foot and a motor having a rotatable power shaft. A brush stem is attached to the power handle and extends therefrom to terminate at a stem head. A brush cartridge is attached to the stem head and extends therefrom to terminate at a toothbrush head. The brush cartridge includes at least one generally cylindrical brush oriented approximately headward-to-footward. A drive shaft extends from the power handle to the brush. A transmission transmits the motion of the power shaft to selectively cause the drive shaft alternatively to rotate about its longitudinal axis and to move parallel thereto in a reciprocating manner. A user of the rotary electric toothbrush thus may direct power from a single motor selectively to cause the brush to rotate about its longitudinal axis and, alternatively, to move in a reciprocating manner parallel thereto.

17 Claims, 8 Drawing Figures

ROTARY ELECTRIC TOOTHBRUSH

TECHNICAL FIELD

The present invention relates to electric toothbrushes in general and, in particular, to electric toothbrushes providing a rotary brushing action.

BACKGROUND OF ART

It is generally known that tooth decay and periodontal disease are at least partially caused by plaque build-up on the surfaces of teeth and gums. Plaque is a sticky, translucent mass composed mainly of bacteria that are able to form long filamentous strands allowing the bacteria to adhere to smooth surfaces of the teeth and gums. These bacteria feed on dissolved sugars, sloughed skin cells, and tissue fluids. They produce waste products, acids and enzymes that are toxic to both tooth enamel and gingival tissues, including the gums, those gingival tissues immediately surrounding the teeth. If left undisturbed for 24-36 hours, the individual plaque bacteria develop into mature colonies that have the capacity to concentrate the acids, isolate them from dilution by the buffering action of saliva, and hold the acids against the tooth surface. If plaque build-up is chronic and sugar consumption is repetitive, the incessant acid insults first demineralize and then cavitate the enamel surface. This cavitation is the process we call dental caries or tooth decay. The toxic enzymes produced by plaque bacteria have the capacity to breakdown connective tissue holding gingival tissue together. If the plaque enzymes contact the gingival tissue of the sulcus area, the V-shaped crevice where the tooth and gum come together, the attachment of the gum to the tooth can loosen and a pocketforms. The depth of this gingival pocket is the pathologic barometer of the severity of periodontal disease.

Both of these pathologic processes (which together account for 98% of tooth loss) can be stopped effectively if plaque is not allowed to remain on the tooth long enough to develop mature colonies. Therefore daily thorough mouth cleaning can substantially prevent these oral diseases from causing tooth loss. Toothbrushing is the most successful widely practiced method of removing plaque from the mouth. The complex anatomy of the teeth and gums requires two distinct brushing motions to remove plaque effectively. Unfortunately, very few people ever master these two brushing motions, which are relatively complex and require a high degree of dexterity. The brushing motions also require more time than most people are willing to spend brushing their teeth.

The first brushing motion is a rolling or rotary brush motion beginning at the gum at the base of the tooth and continuing across the tooth to its biting surface. This rotary or rolling motion is known to be the most effective method of cleaning the tooth surfaces facing the spaces between the teeth known as the interdental spaces. The second brushing motion needed for thorough plaque removal is a series of rapid but very short vibratory strokes. To correctly execute the vibratory motion, the brush is placed along the gum line with some of the bristles gently inserted into the sulcus. The brush handle then is moved back and forth about one-eighth of an inch, with the bristle tips held stationary within the sulcus. This important vibratory motion removes plaque from the otherwise hard to reach sulcus.

Instead of using these effective brushing techniques, most people not only brush their teeth less effectively but actually brush in ways that have pathological consequences. For example, many people brush their teeth with a back and forth sawing motion. This reciprocating motion cleans the broad sides of the teeth but fails to clean in the interdental spaces. Many people try to perform the rotary or rolling motion but make the mistake of going too far with their brush stroke. They start on the upper gum line and brush down over upper teeth, the lower teeth and onto the lower gum line, or just the reverse. This has two pathological effects. First, gingival tissue is pushed away from the teeth, a practice that can lead to premature gingival recession. Second, mouth fluids are swept into the sulcus. Mouth fluids typically contain plaque-forming bacteria and, once lodged in the sulcus, are seldom removed because very few people outside of the dental professional community have mastered the complex, vibratory sulcus cleaning stroke.

The ideal electric toothbrush would safely simulate *both* rotary and vibratory brushing motions. Electric brushes have been designed using a rotary principle with spinning, cylinder-shaped brushes. Rotary toothbrushes having but one brush generally are provided with a reversible motor. The reversible motor is important because, in order to avoid sweeping mouth fluids into the sulcus and pushing gingival tissue away from the tooth, the brush has to spin in a downward direction against upper teeth and in an upward direction against lower teeth. Examples of such toothbrushes include Kurachi, U.S. Pat. No. 3,739,416; Grossman, U.S. Pat. No. 3,551,932; Koblanski, U.S. Pat. No. 3,829,922; Quint, U.S. Pat. No. 4,163,300; Fortenberry, U.S. Pat. No. 3,235,897; Poizat, U.S. Pat. No. 3,161,899; and Glynn, U.S. Pat. No. 2,279,982. Typically, brush direction must be changed many times during a brushing, and it is not easy to remember whether the brush is going in the correct direction relative to gum tissue.

Another arrangement that insures that bristles will be moved in the correct direction is the employment of two, parallel, cylindrical rotary brushes, located side-by-side but counter-rotating so as to rotate in opposite directions. The side of such a pair of rotary brushes on which the bristles are moving toward each other is applied to the teeth, the opposite side often being covered by a shield. By means of this arrangement, the lower gum and teeth are encountered by bristles that are sweeping upwardly, and the upper teeth and gum are encountered by bristles sweeping downwardly. Examples of such toothbrushes include Francolino, U.S. Pat. No. 3,800,350; Merkel, U.S. Pat. No. 2,124,145; and O'Rourke, U.S. Pat. No. 4,304,023. Smith, U.S. Pat. No. 4,313,237; and Caliendo, U.S. Pat. No. 3,925,841, show more complicated devices utilizing three rotary brushes, two adapted to sweep upwardly, one on either side of a row of teeth, and a third to sweep across the chewing surface of the teeth. These three brush designs solve the directional problem in that the brushes always rotate in the correct direction relative to the sulcus. However, the three brush arrangement tends to be fairly large and awkward to use for that reason.

Taylor, U.S. Pat. No. 3,512,201; and Taylor, U.S. Pat. No. 3,512,202, show toothbrushes that appear to be unique in providing for both a rotary brushing action and an independent, reciprocating motion of generally cylindrical brushes moving in a direction parallel to their longitudinal axes. Thus, only the Taylor toothbrushes provide for a powered administration to teeth and gums of both the rotary and vibratory brushing actions considered ideal for thorough plaque removal. The Taylor brushes utilize two motors, one to rotate the brushes and a second to reciprocate them axially.

The art is not cognizant of an electric, rotary toothbrush in which the desirable rotary bristle motion and alternatively selectable reciprocating, axial motion is achievable by use of a single motor.

BRIEF SUMMARY OF THE INVENTION

The present invention is summarized in that a rotary electric toothbrush includes a power handle having a foot and a motor, the motor having a rotatable power shaft. Means are included for supplying electrical power to the motor. A longitudinally extended brush stem is attached to the power handle at a point remote from the foot thereof and extends therefrom to terminate at a stem head. A brush cartridge is attached to the stem head and extends therefrom to terminate at a toothbrush head. Thus, "headward" indicates the direction toward the toothbrush head and "footward" indicates the direction toward the foot. The brush cartridge includes at least one generally cylindrical brush, the longitudinal axis of which is oriented approximately headward-to-footward. A drive shaft extends from the power handle to the brush, the headward end of the drive shaft including means for engaging the brush and transmitting to it the motion of the drive shaft. Transmission means are provided for transmitting the motion of the power shaft to selectively cause the drive shaft alternatively to rotate about its longitudinal axis and to move parallel thereto in a reciprocating manner. As a consequence of the structure recited, a user of the electric toothbrush may direct power from a single motor selectively to cause the brush to rotate about its longitudinal axis and, alternatively, to move in a reciprocating manner parallel thereto.

A primary object of the invention is to provide an electric toothbrush having brushes capable of moving alternatively in a rotary and a reciprocating manner.

A second object of the invention is to provide for such a toothbrush in which a single motor can be used to drive the brushes in either a rotary or a reciprocating manner.

Another object of the invention is to provide such a toothbrush in which the brushes are joined to the motor by drive shafts capable of transmitting power either in a rotary or reciprocating manner.

A further object of the invention is to provide such a toothbrush in which the motor and the oral soft tissues are protected from torque overloads.

A further object of the invention is to provide such a toothbrush having easily replacable brushes.

Yet another object of the invention is to provide for removable brush stems so that each member of a household may use a different brush stem.

A further object of the invention is to provide for two brush head sizes, one for adults and another for children, both of which may be used with a single power handle.

A further object of the invention is to insure that the rotating brushes are always moving in the correct direction relative to gum tissue.

Yet another object of the invention is to provide a brush whose bristle tips can easily reach and clean all teeth in the mouth.

A further object of the invention is to provide a brush that is portable.

Yet another object of the invention is to provide such a toothbrush that is economical to manufacture and durable of design.

A further object of the invention is to provide such a toothbrush in which the speed of operation of the brush is adjustable for operation in each of the two manners of movement referred to.

A further object of the invention is to provide such a toothbrush in which the relative speed of operation in the rotary and reciprocating modes can be preset, independent of adjustments to motor speed.

Other objects, features, and advantages of the invention will be apparent from the following detailed description taken in conjunction with the accompanying drawings showing a preferred embodiment of an electric toothbrush exemplifying the principles of the invention.

DETAILED DESCRIPTION OF THE PREFERRED EMBODIMENT

Figure 1:
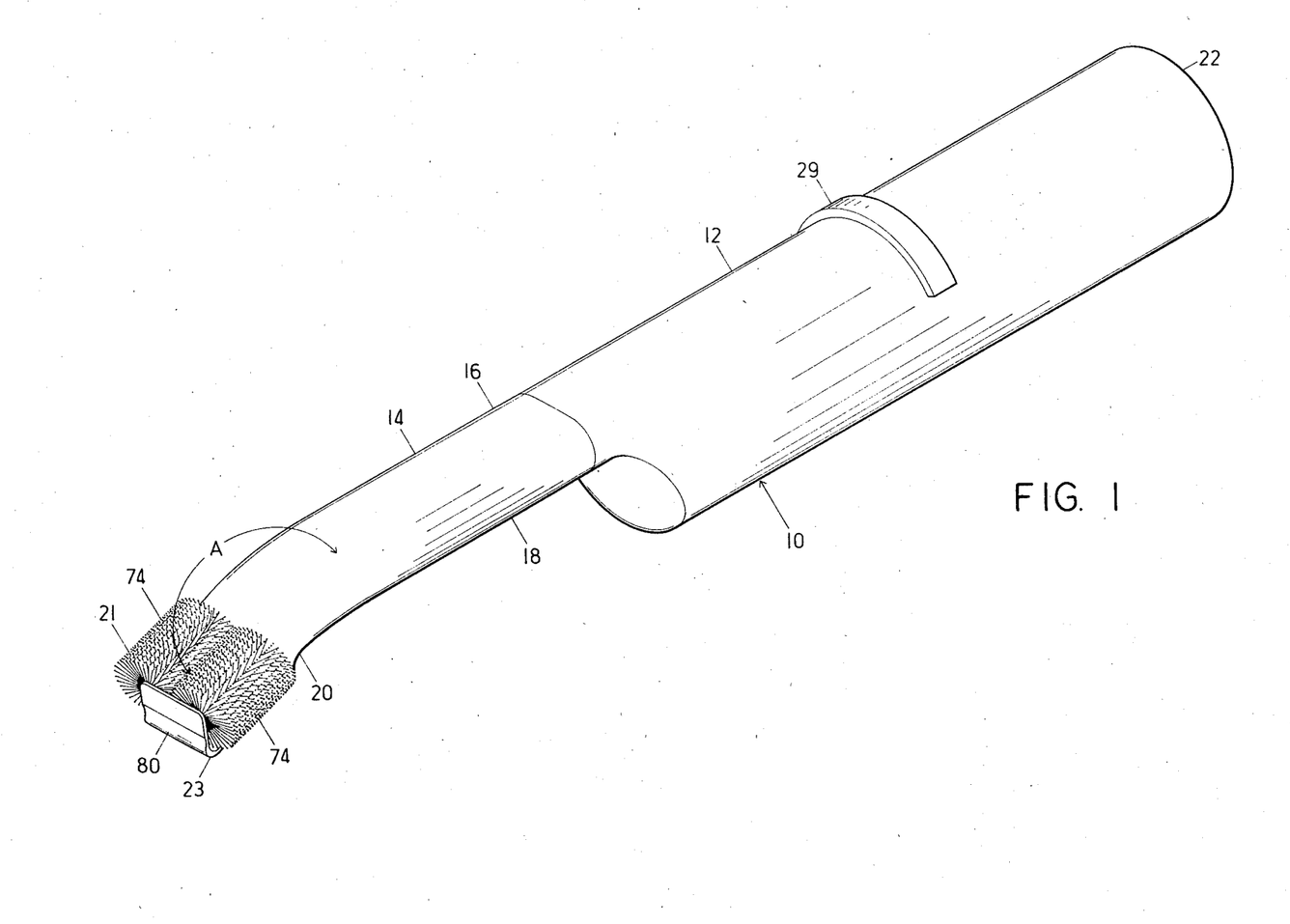
FIG. 1 is an isometric perspective view of a rotary electric toothbrush constructed in accord with the present invention.
Figure 3:
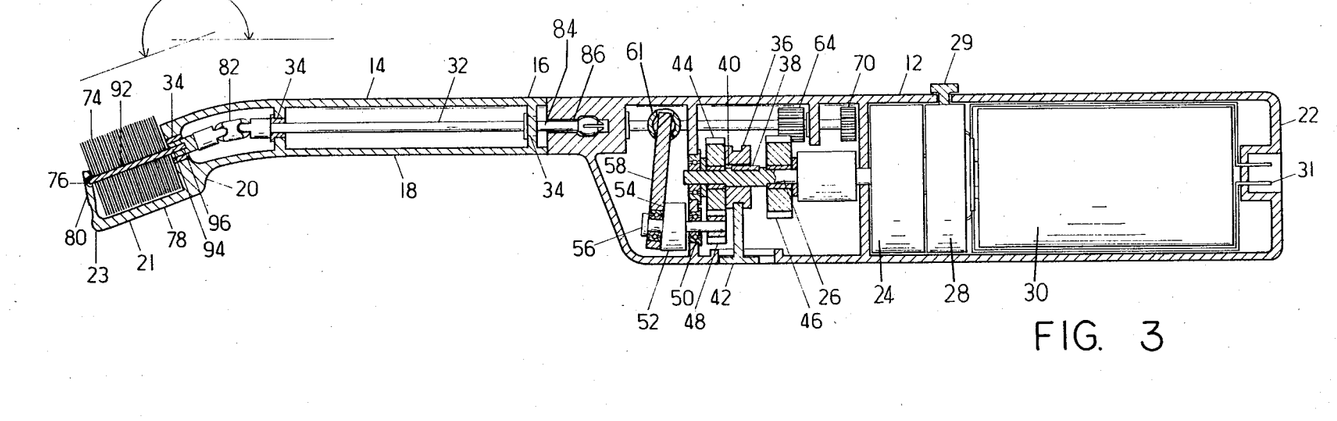
FIG. 3 is a cross-sectional view of the rotary electric toothbrush of FIG. 1 taken along section line 3—3 of FIG. 2.

Referring more particularly to the drawings, wherein like numbers refer to like parts, FIG. 1 shows a first embodiment of an electric toothbrush, generally indicated at 10, constructed in accord with the present invention. The electric toothbrush 10 includes a power handle 12 and a longitudinally extended brush stem 14. Preferably the brush stem 14 is removable from the power handle 12 by means to be discussed below, so that more than one brush stem may be used interchangably with a single power handle. The brush stem 14 has a stem base 16 adjacent to the power handle 12, a stem throat 18, and a stem head 20 remote from the stem base. A brush cartridge 21 is attached to the stem head 20. The brush cartridge 21 may be so attached permanently, constituting a unitary continuation of the brush stem 14, as is shown in FIG. 3. However, as shown in the alternative embodiment of FIG. 5, the brush cartridge also may be removably attached to the brush stem by means for attachment discussed below.

The power handle 12 extends from its point of attachment to the brush stem 14 to terminate at a foot 22. The brush cartridge 21 extends from the stem head 20 to terminate at a toothbrush head 23, which is that portion of the toothbrush 10 most remote from the foot 22. Thus, the parts of the electric toothbrush 10 may be referred to as having "headward" or "footward" ends, portions, movement, and the like.

The electric toothbrush 10 includes an electric motor indicated schematically at 24 in FIG. 3. The motor 24 is located in the power handle 12 and has a rotating power shaft 26 extending headwardly from the motor. In the embodiment of FIG. 3, the motor 24 may be a nonreversing motor and preferably includes means to selectively vary the speed of the motor, such as the rheostat shown at 28 having an externally mounted, finger operable control 29. The electric toothbrush 10 further includes means for supplying electrical power to the motor 24. Preferably a rechargable battery is located in the power handle 12, as is indicated schematically at 30 in FIG. 3. If so, a plug connection such as that shown at 31 in FIG. 3 is provided for connecting the battery 30 to a suitable charging device. However, alternative means for supplying electrical power are clearly possible, such as a power cord extending from the power handle 12 to an external source of electrical power.

At least one and preferably two, rigid drive shafts 32 extend from the vicinity of the power shaft 26 in the power handle 12 toward the toothbrush head 23. The drive shafts 32 are supported by bearings such as the sleeve bearings shown at 34 that include means to allow the drive shafts both to rotate and to move in a reciprocating manner parallel to the longitudinal axes of the drive shafts. To accomodate such bearings 34, the drive shafts 32 preferably are cylindrical.

Figure 4:
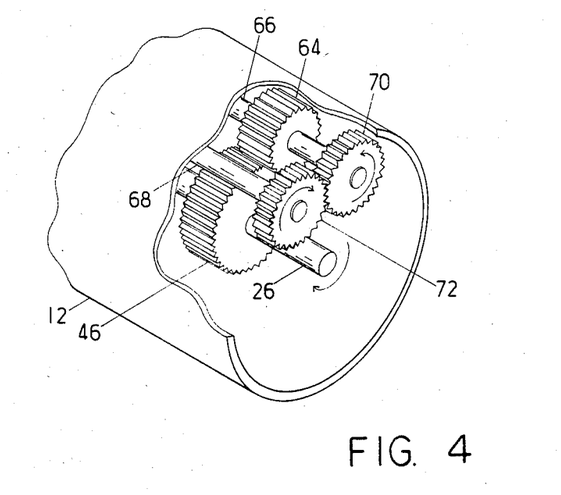
FIG. 4 is an isometric perspective view of a portion of the power handle of the rotary electric toothbrush of FIG. 1, with various parts broken away.

Transmission means are provided for transmitting the motion of the power shaft 26 to the drive shafts 32 to selectively cause the drive shafts either to rotate or to move in a reciprocating manner, as described. A variety of such transmission means are possible. In the first embodiment, as shown in FIGS. 3 and 4, a magnetic clutch plate 36 is allowed to slide longitudinally on the power shaft 26 within a limited range. The magnetic clutch plate 36 is forced to rotate with the power shaft 26 by means of a key 38. The key 38 extends parallel to the longitudinal axis of and is rigidly mounted on the power shaft 26. The magnetic clutch plate 36 includes a longitudinally extending slot 40 having a size sufficient to allow the clutch plate to move freely over the key 38 but only in a direction parallel to the longitudinal axis of the power shaft 26. A mode selector switch 42 is adapted to move the clutch plate 36 longitudinally along the power shaft 26 to selected locations thereon.

First and second freely turning gears 44, 46 are mounted on the power shaft 26 in freely turning relation thereto, the first freely turning gear 44 being located headwardly of the magnetic clutch plate 36 and the second freely turning gear 46 being located footwardly therefrom. Each of the freely turning gears 44, 46 are restrained from substantial movement longitudinally on the power shaft 26. The freely turning gears 44, 46 are made of ferromagnetic material. Consequently, when the mode selector switch 42 is utilized to move the magnetic clutch plate 36 into contact with one of the freely turning gears 44, 46, the clutch plate becomes magnetically engaged therewith, tending to turn that freely turning gear but capable of slipping thereon if the torque necessary to turn the freely turning gear exceeds a selected amount. Thus, the transmission includes protective means for protecting the motor 24 and oral soft tissues in the event the freely turning gears 44, 46 become jammed or stalled. Although the magnetic clutch plate 36 is preferred, a comparable and equivalent clutch plate arrangement may be designed using springs instead of magnetism to force the clutch plate against the freely turning gears 44, 46. Such alternatives are within the spirit and scope of the invention.

The first freely turning gear 44 is engaged with a first driven gear 48. The first driven gear 48 turns a secondary power shaft 50 on which is mounted a headwardly facing swash plate 52. The longitudinal axis of the swash plate 52 is oriented generally parallel to the longitudinal axes of the drive shafts 32. The swash plate 52 has a generally headwardly facing driving surface 54 canted to the longitudinal axis of the swash plate. A crank pivot pin 56 extends generally headwardly at right angles to the driving surface 54. A longitudinally extended crank rod 58 is engaged over the crank pivot pin 56 in freely turning relation thereto. It will be apparent that, as a consequence of this structure, portions of the crank rod 58 remote from the crank pivot pin 56 will reciprocate in a headward-to-footward direction when the swash plate 52 is rotated and the crank rod is restrained from rotating with it.

A stroke plate 60 is attached to the crank rod 58 at a point remote from the crank pivot pin 56. The crank rod 58 is attached to the stroke plate 60 both in freely pivoting relation, preferably by means of a spherical bearing, and with freedom to move relative to the stroke plate in a direction parallel to the longitudinal axis of the crank rod 58, preferably by means of a sleeve bearing or the like. The spherical and sleeve bearings may be parts of a single complex bearing, such as the stroke plate bearing indicated at 61 in FIG. 3.

As the swash plate 52 rotates, the stroke plate 60 is driven alternately headwardly and footwardly in a reciprocating manner. The stroke plate 60 is attached to each of the drive shafts 32 by bearings that allow the drive shafts to rotate freely with respect to the stroke plate about their longitudinal axes but that prevent movement of the drive shafts relative to the stroke plate in a direction parallel to their longitudinal axes. Preferably the drive shafts 32 each have a section of reduced diameter, shown in phantom in FIG. 2 at 62. The stroke plate 60 then may be attached to the drive shafts 32 by drive shaft sleeve bearings 63 (shown in phantom in FIG. 2) adapted to fit within the sections of reduced diameter 62, thereby preventing movement of the stroke plate relative to the drive shafts 32 in a direction parallel to their longitudinal axes. Thus, with the magnetic clutch plate 36 moved into contact with the first freely turning gear 44, the drive shafts 32 move axially in a reciprocating fashion as the power shaft 26 of the motor 24 turns.

The second freely turning gear 46 turns a second driven gear 64. The second driven gear 64 is attached to a first one of the drive shafts 32, which shall be referred to as the "primary drive shaft," shown in FIG. 4 at 66. The remaining drive shaft 32 shall be referred to as the "secondary drive shaft," indicated in FIG. 4 at 68. A driving coordinating gear 70 is attached to the primary drive shaft 66 and turns with it. A driven coordinating gear 72 is attached to the secondary drive shaft 68 and is driven by the driving coordinating gear 70. As a consequence of this arrangement, the primary and secondary drive shafts 66, 68 rotate about their longitudinal axes in opposite directions.

The brush cartridge 21 includes at least one and preferably two, generally cylindrical brushes 74. The cylindrical brushes 74 are located side by side and preferably intermesh slightly. The brushes 74 are attached by their footward ends to the headward-most ends of the drive shafts 32 and are driven by them. The headward end of each of the brushes 74 is mounted in an end bearing 76 that includes means to allow the brushes to rotate freely about their longitudinal axes and also to move axially in a reciprocating manner. Preferably the brush cartridge 21 includes a shield member 78 extending from the footward-most end of the brush cartridge first to one side and then headwardly beyond the brushes 74. An end cap 80 extends from the shield member 78 across a selected portion of the headward-most end of the brushes 74. Preferably the end cap 80 is hingedly attached to the shield member 78, allowing portions of the end cap to move headwardly and footwardly. Thus, the end cap 80 and shield member 78 may be unitarily molded, linked by a thinned, molded web capable of flexing in a hinge-like manner, such structures being known in the art as "living hinges." The end cap 80 is biased toward the footward direction and holds the end bearings 76 on footwardly facing surfaces thereof. As a consequence of this arrangement, the end bearings 76 are biased against the headward ends of the brushes 74 but also can be resiliently forced headwardly by the brushes when the brushes are in their reciprocating mode.

The structure just described is that preferred as a brush support means for supporting the brushes 74 so as to accommodate both axial and rotary brush movement. Other, alternative support means are possible. Thus, the shield member 78 could be telescoping in a headward-to-footward direction, biased toward a shorter length. With such an arrangement, the end cap 80 could be rigidly joined to the shield member 78 and still be footwardly biased. Alternatively, the brushes 74 could be made stiff enough not to require support at both the headward and footward end. In such an arrangement, the attachment of the brushes 74 to the drive shafts 32 would have to be sufficiently secure to draw the brush footwardly when in the reciprocating mode without the aid of a footwardly biased end cap 80. Alternatively, brushes 74 so attached to the drive shafts 32 could receive lateral support from appropriate bearings in an end cap 80 without the need of a footwardly biased end cap. It is apparent that many alternative designs for brush support means are possible, all of which are within the scope and spirit of the invention.

It is known to be advantageous to have the cylindrical brushes of a rotary toothbrush so oriented that that side of the cylindrical brush or brushes intended to contact the teeth of a user is tipped slightly endwardly, away from the remaining parts of the electric toothbrush. Thus, it is preferred that the longitudinal axes of the cylindrical brushes 74 be oriented at an angle "A" in excess of 180° to the longitudinal axis of the brush stem 14, as is shown in FIGS. 1 and 3. Similarly, it is sometimes advantageous that the angle "A" be less than 180° (not shown) so that the side of the brushes 74 intended to contact the user's teeth is tipped footwardly. To accommodate either arrangement in which the longitudinal axes of the brushes are oriented to the longitudinal axis of the brush stem at an angle of other than 180°, the drive shafts 32 must be capable of negotiating a bend generally near the stem head 20. Various designs for flexible rotating shafts are possible. However, the drive shafts 32 must also be capable of transmitting to the cylindrical brushes 74 the reciprocating movement impartable to the drive shafts by the movement of the crank rod 58, discussed above. Consequently, each drive shaft 32 includes means for transmitting both torque and axially directed force.

Various structures are possible for a drive shaft 32 including means for transmitting both torque and axially directed force. For example, flexible wire shafts contained within sleeves or woven cable shafts would be suitable. In the first embodiment as shown in FIG. 3, the drive shafts 32 each are equipped with two universal joints, each universal joint inserted into the drive shaft and separated from each other by a substantially rigid portion of the drive shaft, which arrangement shall be referred to herein as a double universal joint, as shown at 82 in FIG. 3. The double universal joint 82 is located approximately at the stem head 20. The sleeve bearings 34 include bearings located immediately headwardly and footwardly of the double universal joints 82, as is indicated in FIG. 3. The double universal joints 82 are capable of efficiently transferring both rotary and axial motion, allowing the brushes 74 to rotate or to reciprocate axially in response to the transmission means for transmitting the motion of the power shaft 26 to the drive shafts 32, as disclosed above.

As is mentioned above, the brush stem 14 preferably is entirely removable from the power handle 12 being joined thereto by stem attachment means for removably attaching the brush stem to the power handle. The stem attachment means may have any of various possible structures, one of which is shown in the first embodiment. Alternative stem attachment means will be discussed below, but in general such attachment means includes means for stabilizing the joint and means for releasably interlocking separable portions of the drive shafts 32.

Figure 2:
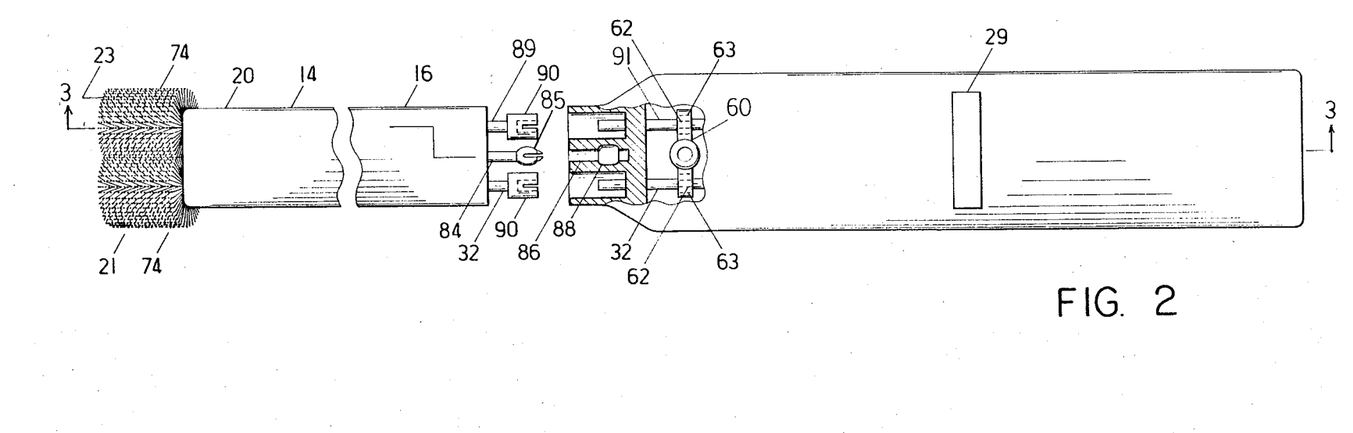
FIG. 2 is a top plan view of the rotary electric toothbrush of FIG. 1 with the stem disengaged from the power handle and certain parts of the power handle broken away.

In the first embodiment, as shown in FIGS. 2 and 3, the brush stem 14 has an engagement prong 84. The engagement prong 84 extends footwardly from the footward-most end of the brush stem 14 in a direction generally parallel to the drive shafts 32. An engagement well 86 is formed in the headward-most end of the power handle 12 and is adapted to receive the engagement prong 84. Preferably the footward end 85 of the engagement prong 84 is oversized with respect to the engagement well 86, slotted, and made of a resilient material so that the footward end of the engagement prong is compressed upon insertion into the engagement well. The engagement well 86 may include an enlarged portion 88 in which the oversized end 85 of the engagement prong 84 may be received and may expand to hold the engagement prong within the engagement well. The engagement prong 84 and associated structures are an example of means for joint stabilization.

The drive shafts 32 are separable into brush stem portions 89 and power handle portions 91. The brush stem and power handle portions 89, 91 of the drive shafts 32 are equipped with press-fit engagement devices such as the split resilient collars shown at 90 in FIG. 2. The split collars 90 are rigidly attached to one portion of the drive shaft 32 and are adapted to slip over the end of the other portion of the drive shaft in resiliently clamping relation. The split collars 90 and associated structures described are an example of means for releasably interlocking separable portions of the drive shafts 32.

Preferably the brushes 74 are removable from the brush cartridge 21. Thus, each brush 74 may include a central spindle 92 terminating in a footwardly extending, flattened spade end 94. The headward-most ends of the drive shafts 32 each may be equipped with a headwardly opening brush slot 96 capable of receiving and holding the spade end 94 of a brush 74. The end bearings 76 may include means to releasably hold the headward ends of the brushes 74, so that a user may pull the end cap 80 headwardly until the headward ends of the brushes 74 may be slipped out of the end bearings 76 and the spade ends 94 of the central spindles 92 withdrawn from the brush slots 96. This action may be reversed to install a brush 74.

Figure 5:
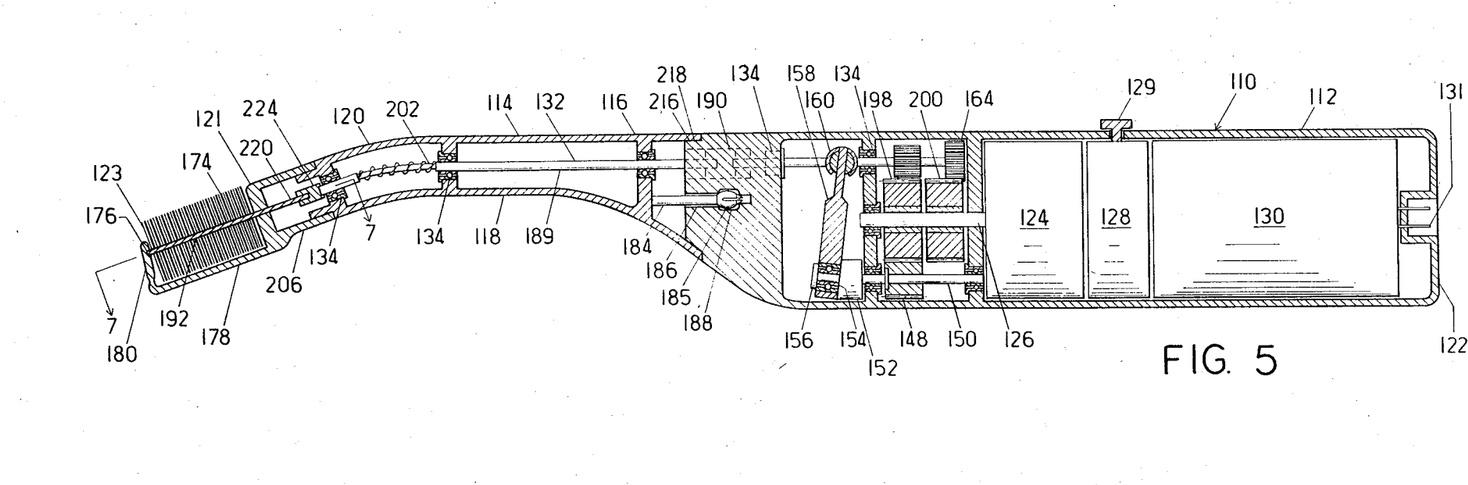
FIG. 5 is a cross-sectional view of a second embodiment of the rotary electric toothbrush of the invention, the view generally corresponding to FIG. 3.
Figure 6:
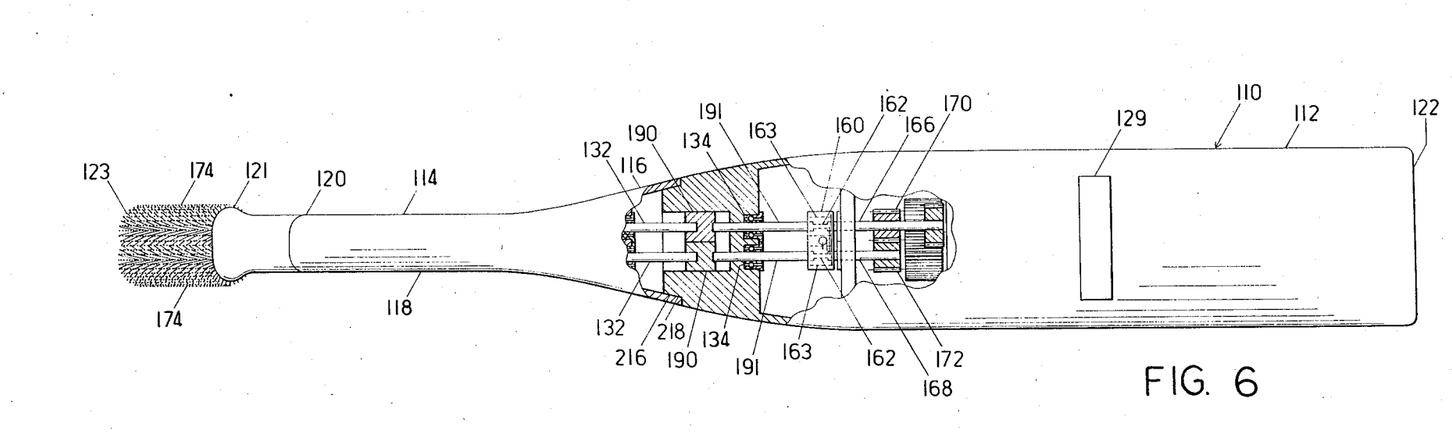
FIG. 6 is a top plan view of the rotary electric toothbrush of FIG. 5, the view corresponding generally to FIG. 2.

A second embodiment of an electric toothbrush constructed in accord with the invention is shown at 110 in FIGS. 5 and 6. The second embodiment 110 has many parts that are essentially the same as the corresponding parts of the first embodiment shown at 10, as described above. Corresponding parts of the second embodiment will be given corresponding reference numbers except that those reference numbers shall be higher than the reference numbers of the first embodiment by 100. Thus, the second embodiment 110 has a power handle 112 corresponding to the power handle 12 of the first embodiment 10, and so forth. The function and structure of these corresponding parts will not be separately discussed. Parts of the second embodiment discussed and not having a corresponding part in the first embodiment all will have reference numbers at least as great as 198.

The transmission means of the second embodiment 110 for transmitting the motion of the power shaft 126 to the drive shafts 132 to selectively cause the drive shafts to rotate or to move in a reciprocating manner is an illustration of one of several alternative embodiments of suitable transmission means. The transmission means of the second embodiment cooperates with a motor 124 having a power shaft 126. Unlike the otherwise corresponding motor 24 of the first embodiment, the motor 124 of the second embodiment is electrically reversible. The transmission means of the second embodiment includes first and second, conventional, one way clutch-driven gears 198, 200. The first one way clutch-driven gear 198 includes means for engaging the power shaft 126 exclusively when the power shaft is turning in a first direction. The second one way clutch-driven gear 200 includes means for engaging the power shaft 126 exclusively when the power shaft is turning in the opposite direction.

The first one way clutch-driven gear 198 is engaged with a first driven gear 148. The first driven gear 148 is mounted on a secondary power shaft 150 having a swash plate 152 associated with a crank rod 158, stroke plate 160, and so forth, in the same manner as the corresponding and associated parts are related in the first embodiment 10 disclosed above. Thus, when the power shaft 126 rotates in the first direction, the first one way clutch-driven gear 198 engages the power shaft 126 and is turned thereby, causing the drive shafts 132 to move in a reciprocating manner.

The second one way clutch-driven gear 200 is engaged with a second driven gear 164 corresponding to the second driven gear 64 of the first embodiment. The second driven gear 164 is mounted on a primary drive shaft 166. A secondary drive shaft 168 is caused to rotate in a direction opposite to the rotational direction of the primary drive shaft 166 by the interaction of driven and driving coordinating gears 170, 172, having the same structure and mode of interaction as the corresponding parts of the first embodiment. Thus, when the power shaft 126 rotates in the direction opposite to the first direction referred to above, the second one way clutch-driven gear 200 engages the power shaft 126, causing the drive shafts 132 to rotate about their longitudinal axes.

The second embodiment includes reversing means for reversing the direction of rotation of the motor 124. By the mechanisms described above, the reversing means effectively allows a user to select between a rotary and a reciprocating brush motion. The reversing means may include a separate reversing switch or, as is preferred, may be incorporated in the rheostat 128 by which the speed of the motor 124 is also controlled. It will be apparent that, with both the first and second embodiments, a user may select between rotary and reciprocating modes of operation and separately may select the speed of operation in either mode. In addition, the gear ratios between the driven gears 48, 64, 148, 164 and those gears driving them may be adjusted so as to provide a desirable relationship between the speed of rotation of the brushes 74, 174 and the rate at which they reciprocate at any given motor speed. If desired for overload protection, a conventionally designed, spring-loaded, slipping clutch may be inserted in the transmission means at any convenient location.

Each of the particular transmission means described utilized a swash plate 52, 152 and an attached crank rod 58, 158 and stroke plate 60, 160 to transform the circular motion of the secondary power shaft 150 into a reciprocating motion. However, many mechanical means for translating rotary motion to reciprocal motion are known to those skilled in the art. For example, cams of various sort may be rotated by a shaft and drive a cam follower in a manner that is either directly reciprocating or that may be transformed into a reciprocating motion by a suitable linkage. The mechanical means for translating rotary motion into reciprocating motion shown is that preferred, but alternative means, including those referred to, clearly fall within the scope and spirit of the present invention.

Figure 8:
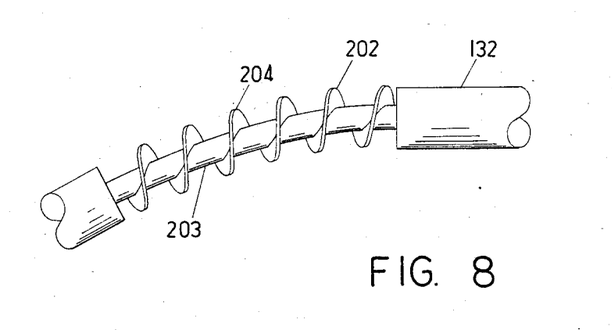
FIG. 8 is a side elevation of a flexible portion of a drive shaft.

The drive shafts 132 of both embodiments 10 and 110 are adapted to be unitarily molded from a plastic or other flexible, moldable material. The drive shafts 132 each include means for transmitting both rotary and axially directed motion that are an alternative means to the double universal joint 82 employed in the drive shafts 32 shown as part of the first embodiment 10. Each drive shaft 132 of the second embodiment includes a flexible portion 202 of the drive shaft, best seen in FIG. 8. The flexible portion 202 has a central shaft 203 and a helicoid member 204 having a diameter greater than that of the central shaft. The helicoid member 204 extends for the full length of the flexible portion 202. The flexible portion 202 exhibits a reduced resistance to lateral flexing when compared to the remaining portions of the drive shaft 132. However, the central shaft 203 effectively transmits force directed axially thereto, and the helicoid member 204 effectively transmits torque.

Figure 7:
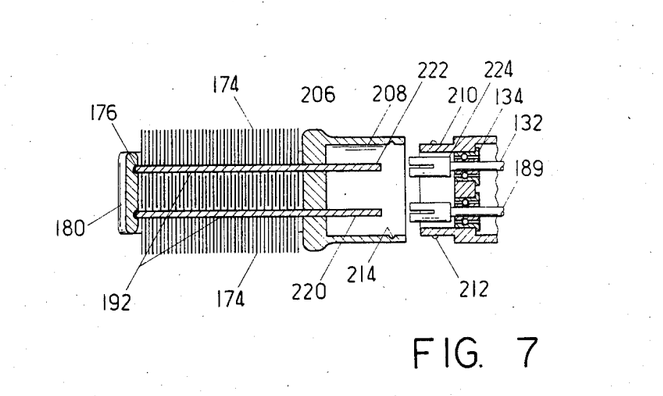
FIG. 7 is a cross-sectional view of the brush cartridge taken along section lines 7—7 of FIG. 5.

It has been noted above that the brush cartridge may be formed unitarily with the stem, as it is shown at 21 and 14 in the first embodiment 10. However, the brush cartridge also may be separable from the stem, as is shown in the second embodiment 110 at 121 and 114 with a joint thus established therebetween. In that event, cartridge attachment means are provided for releasably attaching the cartridge 121 to the stem head 120. The cartridge attachment means is generally analogous to the stem attachment means discussed above with relation to the first embodiment 10. Thus, it includes means for stabilizing the joint and means for releasably interlocking separable portions of the drive shafts. The cartridge attachment means may be physically analogous to the particular stem attachment means disclosed above with respect to the first embodiment 10, with an engagement prong, engagement well, and resilient split collars or comparable means for releasably interlocking separable portions of the drive shafts. However, the preferred embodiment of the cartridge attachment means is that shown as part of the second embodiment 110 of the electric toothbrush, as seen in FIGS. 5 and 7.

As shown in those figures, the means for joint stabilization includes a joint sleeve 206 extending footwardly from the footwardmost end of the brush cartridge 121. Interior surfaces of the joint sleeve 206 define a footwardly opening joint socket 208. The joint socket 208 is non-round in lateral cross-sectional shape and preferably oval, trapezoidal, or the like. A male socket member 210 extends headwardly from the stem head 120. The male socket member 210 has a size and cross-sectional shape so selected that the male socket member may slide snugly in and out of the joint socket 208. Because of the non-round cross-sectional shape of the joint socket 208, the male socket member 210 is restrained from axial rotation within the joint socket.

An entirely equivalent structure is obtainable by forming a joint socket at the headward end of the brush stem and a male socket member at the footward end of the brush cartridge.

Preferably detent means are provided for releasably retaining the male socket member 210 within the joint socket 208. In the embodiment shown in FIGS. 5 and 7, the male socket member 210 has a ridge 212, and the joint socket 208 includes a groove 214, the ridge and groove being so positioned and having a size such that, when the male socket member is inserted into the joint socket, the ridge resiliently snaps into the groove to be releasably retained therein.

The brush cartridge 121 of the second embodiment 110 has cylindrical brushes 174 generally comparable to the cylindrical brushes 74 of the first embodiment 10. Thus, the cylindrical brushes 174 each have a brush central spindle 192 that is continuous with a portion 220 of the associated drive shaft 132 separable from the brush stem portion 189 of the drive shaft. The footward end of each central spindle 192 extends into the joint socket 208, terminating in a round end 222. The brush stem portion 189 of each drive shaft 132 terminates at the stem head 120 and has a resilient split collar 224 opening headwardly. When the brush cartridge 121 is attached to the stem head 120 by insertion of the male socket member 210 into the joint socket 208, the round ends 222 may be engaged in the split collars 224 to be removably engaged thereby. The round ends 222 and split collars 224 are an example of means for releasably interlocking the separable brush cartridge portions 220 and the brush stem portions 189 of the drive shafts 132.

It will be apparent that, as a consequence of the structure referred to above, the brushes 174 of the rotary electric toothbrush 110 may quickly and easily be changed. Furthermore, the brushes 174 may be changed by a person of only modest manual dexterity. Individual brushes need not be handled or placed in an exacting relationship to other parts. Instead, the entire brush cartridge 121 may simply be unplugged and replaced with a new one. Furthermore, by this arrangement, brush cartridges 121 of different sizes may be employed with a single brush stem 114, making it possible for a user to select among brushes of differing stiffness or abrasive characteristics or to select larger or smaller sizes of the brush cartridge. Thus, brush cartridges 121 may be furnished in small, pediatric sizes as well as in larger, adult sizes. Furthermore, the end cap 180 of the brush cartridge 121 need not be able to endure as wide a range of motion as was described as necessary for the corresponding structure of the first embodiment of an electric toothbrush identified above at 10. The end cap 180 of the second embodiment 110 of the electric toothbrush is capable of resiliently flexing in hinged relation to the shield member 178 as the brushes 174 are moved in a reciprocating manner. However, once the brushes 174 are mounted within the brush cartridge 121 at the time of manufacture, it is unnecessary subsequently to replace them. Instead, the entire brush cartridge 121 may be discarded and replaced with a new one.

As is discussed above, the stem attachment means described with respect to the first embodiment 10 of the electric toothbrush of the invention and the cartridge attachment means, a particular example of which has just been described as part of the second embodiment 110, are deemed to be structural equivalents. The two particular structures described could be exchanged for each other and for other equivalent attachment means that include means for joint stabilization and means for releasably interlocking separable portions of the drive shafts. For example, the stem attachment means illustrated in the figures showing the second embodiment 110 combines features of each of the particular structures just referred to. Thus, an engagement prong 184 extends footwardly frm the stem base 116 and terminates in a resiliently compressible oversized end 185. The power handle 112 has an engagement well 186 opening headwardly and having an enlarged portion 188, all adapted to receive the engagement prong 184. All of these structures correspond to the engagement prong 84 and engagement well 86 of the first embodiment 10 of the electric toothbrush of the invention. Furthermore, the drive shafts 132 are equipped with resilient split collars 190 adapted to function in a manner corresponding to the split collars 90 of the first embodiment 10 of the toothbrush of the invention.

However, it will be observed from the drawings that the relative location of the engagement prong 184 and the drive shafts 132 is somewhat different than that of the corresponding parts of the first embodiment 10. Furthermore, the stem attachment means of the second embodiment 110 of the toothbrush of the invention further includes a stem joint socket 216 formed at the stem base 116 of the brush stem 114 and opening footwardly. The headwardmost end of the power handle 112 has a male power handle socket member 218 adapted to snugly fit within the stem joint socket 216. These two parts have corresponding, noncircular cross-sectional shapes, so that the power handle male socket member 218 cannot turn within the stem joint socket 216. All of these features correspond to the joint socket 208 and male socket member 210 described above as part of the cartridge attachment means. These and all comparable stem and cartridge attachment means are within the scope and spirit of the invention.

All rigid parts of both embodiments described above of the electric toothbrush of the invention may be manufactured from any suitable, rigid material. Most such parts may be conveniently molded from suitable plastics while others may be machined from metals, all by known and conventional techniques. It is understood that the present invention is not limited to the particular construction, materials, and arrangement of parts illustrated and disclosed above. Indeed, with the above disclosure in hand, various equivalent and alternative structures will be apparent to one skilled in the art. Therefore, the invention embraces all such modified forms thereof as come within the scope of the following claims.

What is claimed is:

1. A rotary electric toothbrush comprising:
   a. a power handle having a foot and a motor, the motor having a rotatable power shaft;
   b. means for supplying electrical power to the motor;
   c. a longitudinally extended brush stem attached to the power handle at a point remote from the foot and extending therefrom to terminate at a stem head;
   d. a brush cartridge attached to the stem head and extending therefrom to terminate at a toothbrush head, so that "headward" indicates a direction toward the toothbrush head and "footward" indicates a direction toward the foot, the brush cartridge including at least one generally cylindrical brush the longitudinal axis of which is oriented approximately headward-to-footward;
   e. a drive shaft extending from the power handle to the brush, the headward end of the drive shaft including means for engaging the brush and transmitting to it the motion of the drive shaft; and
   f. transmission means for transmitting the motion of the power shaft to selectively cause the drive shaft alternatively to rotate about its longitudinal axis or to move parallel thereto in a reciprocating manner, whereby a user of the electric toothbrush may direct power from a single motor selectively to cause the brush to rotate about its longitudinal axis and, alternatively, to move in a reciprocating manner parallel thereto.

2. The rotary electric toothbrush of claim 1 wherein the transmission means includes:
   a. first and second freely turning gears mounted on the power shaft;
   b. means for selectively engaging the first and second freely turning gears to cause them to turn with the power shaft;
   c. a first driven gear driven in geared relation by the first freely turning gear;
   d. a swash plate turning with the first driven gear and having a longitudinal axis generally parallel to that of the drive shaft, the swash plate having a driving surface canted with respect to the longitudinal axis of the swash plate;
   e. a crank rod held against the canted driving surface with the canted driving surface freely rotatable with respect to the crank rod, whereby, when the swash plate turns and the crank rod is restrained from turning with its, parts of the crank rod remote from the longitudinal axis of the swash plate move in a reciprocating manner in a direction parallel to the longitudinal axis of the swash plate;
   f. means for pivotably connecting the crank rod at a point remote from the longitudinal axis of the swash plate to the drive shaft, the drive shaft being connected thereto at a fixed point on the longitudinal axis of the drive shaft and the drive shaft remaining free with respect to the crank rod to rotate about the longitudinal axis of the drive shaft, whereby when the first freely turning gear is caused to turn with the power shaft, the drive shaft is thereby made to move parallel to its longitudinal axis in a reciprocating manner; and
   g. a second driven gear driven in geared relation by the second freely turning gear, the second driven gear being mounted on the drive shaft in fixed relation thereto, whereby, when the power shaft is caused to drive the second freely turning gear, the drive shaft rotates about its longitudinal axis.

3. The rotary electric toothbrush of claim 2 wherein the drive shaft is a primary drive shaft and a secondary drive shaft extends parallel thereto, each drive shaft engagable with a brush, the electric toothbrush further comprising:
   a. a driving coordinating gear mounted on the primary drive shaft and turning therewith;
   b. a driven coordinating gear driven by the driving coordinating gear in geared relation thereto and mounted on the secondary drive shaft, turning therewith, whereby the primary and secondary drive shafts rotate about their longitudinal axes in opposite directions; and
   c. means to transmit reciprocating motion of the crank rod to both drive shafts.

4. The rotary electric toothbrush of claim 2 wherein the first and second freely turning gears are made of ferromagnetic material and wherein the means for selectively engaging the first and second freely turning gears to cause them to turn with the power shaft includes a magnetic clutch plate mounted on the power shaft with freedom to slide longitudinally with respect thereto; means to constrain the magnetic clutch plate to rotate with the power shaft; and means to move the clutch plate longitudinally along the power shaft alternatively to magnetically engage the first and second freely turning gears to selectively engage them and cause them to turn with the power shaft.

5. The rotary electric toothbrush of claim 1 including means for selectively reversing the direction of rotation of the rotatable power shaft, and wherein the transmission means includes:
   a. first and second one way, clutch-driven gears mounted on the power shaft, the first one way, clutch-driven gear including means to engage and move with the power shaft exclusively when the power shaft is moving in a first direction, and the second one way, clutch-driven gear including means to engage and turn with the power shaft exclusively when the power shaft is moving in the opposite direction;
   b. a first driven gear engaging the first one way, clutch-driven gear in geared relation;
   c. a swash plate turning with the first driven gear and having a longitudinal axis generally parallel to that of the drive shaft, the swash plate having a driving surface canted with respect to the longitudinal axis of the swash plate;
   d. a crank rod held against the canted driving surface with the canted driving surface freely rotatable with respect to the crank rod, whereby, when the swash plate turns and the crank rod is restrained from turning with it, parts of the crank rod remote from the longitudinal axis of the swash plate move in a reciprocating manner in a direction parallel to the longitudinal axis of the swash plate;

e. means for pivotably connecting the crank rod at a point remote from the longitudinal axis of the swash plate to the drive shaft, the drive shaft being connected thereto on a fixed point on the longitudinal axis of the drive shaft and the drive shaft remaining free with respect to the crank rod to rotate about the longitudinal axis of the drive shaft, whereby when the power shaft so turns as to be engaged by the first one way, clutch-driven gear, the drive shaft is thereby made to move parallel to its longitudinal axis in a reciprocating manner; and f. a second driven gear driven in geared relation by the second one way, clutch-driven gear, the second driven gear being mounted on the drive shaft in fixed relation thereto, whereby, when the power shaft so turns as to be engaged by the second one way, clutch-driven gear, the drive shaft rotates about its longitudinal axis.

6. The rotary electric toothbrush of claim 5 wherein the drive shaft is a primary drive shaft and secondary drive shaft extends parallel thereto, each drive shaft engageable with a brush, the electric rotary toothbrush further comprising:

a. a driving coordinating gear mounted on the primary drive shaft and turning therewith;

b. a driven coordinating gear driven by the driving coordinating gear in geared relation thereto and mounted on the secondary drive shaft, turning therewith, whereby the primary and secondary drive shafts rotate about their longitudinal axes in opposite directions; and c. means to transmit reciprocating motion of the crank rod to both drive shafts.

7. The rotary toothbrush of claim 1 wherein the brush cartridge is attached to the stem head by cartridge attachment means for releasably attaching the cartridge to the stem head to create a joint therebetween, the drive shaft being separable into a stem portion and a brush cartridge portion, the cartridge attachment means including means for stabilizing the joint and means for releasably interlocking the stem and brush cartridge portions of the drive shaft.

8. The rotary electric toothbrush of claim 7 wherein the means for stabilizing the joint includes:

a. surfaces of the brush cartridge defining a joint socket having a non-round cross-sectional shape and opening footwardly;

b. a male socket member located at the headwardmost end of the brush stem and corresponding in cross-sectional shape to the joint socket, whereby the male socket member is receivable within the joint socket in non-turning, mating relation; and c. detent means for releasably retaining the male socket member within the joint socket.

9. The rotary toothbrush of claim 1 including stem attachment means for removably attaching the brush stem to the power handle to create a joint therebetween, the drive shaft being separable into a brush stem portion and a power handle portion, the stem attachment means including means for stabilizing the joint and means for releasably interlocking the brush stem portion and power handle portion of the drive shaft.

10. The rotary electric toothbrush of claim 9 wherein the means for stabilizing the joint includes an engagement prong extending from one of the brush stem and the power handle and an engagement well included in the other of the brush stem and power handle, the engagement well including means to receive the engagement prong in removable, mating relation.

11. The rotary electric toothbrush of claim 1 wherein the longitudinal axis of the cylindrical brush is oriented at an angle to the longitudinal axis of the brush stem that is other than 180° so that a side of the cylindrical brush is presented one of endwardly and footwardly to a selected degree, and the drive shaft includes means for transmitting both torque and longitudinally directed force to the brush so oriented.

12. The rotary electric toothbrush of claim 11 wherein the means for transmitting both torque and longitudinally directed force includes a double U joint.

13. The rotary electric toothbrush of claim 11 wherein the means for transmitting both torque and longitudinally directed force includes a flexible portion of the drive shaft having a central shaft having a lesser cross section than that of contiguous portions of the drive shaft, to provide for lateral flexibility of the flexible portion of the drive shaft, and a continuous, helicoid member extending for the length of the central shaft and fastened at each end thereof to the contiguous portions of the drive shaft, whereupon torque may be transmitted across the flexible section of the drive shaft.

14. The rotary electric toothbrush of claim 1 wherein the brush cartridge includes a shield member extending from the footwardmost end of the brush cartridge headwardly beyond the brush, and an end cap extending from the shield member across a selected portion of the headwardmost end of the brush, the end cap being hingedly attached to the shield member and resiliently biased toward the footward direction, the end cap having an end bearing on footwardly facing surfaces thereof, said end bearing being biased against the headwardmost end of the brush with the brush held in freely turning relation thereto, whereby the end cap may be resiliently forced headwardly by the brush when the brush is moving in a reciprocating manner.

15. The rotary electric toothbrush of claim 14 wherein the end cap and shield member are unitarily molded and joined by a living hinge.

16. The rotary electric toothbrush of claim 14 wherein the headwardmost portion of the brush is releasably engaged in the end bearing, the brush includes a brush central spindle extending along the longitudinal axis thereof, and the rotary electric toothbrush further comprises means for releasably engaging the footwardmost end of the brush spindle with the headwardmost end of the drive shaft, whereupon a user of the rotary electric toothbrush may manually flex the end cap headwardly, disengaging the brush from the end bearing, and freely remove and replace the brush.

17. The rotary electric toothbrush of claim 1 further comprising means for adjustably selecting the speed of the motor, whereby the speed of rotation of the brush and the frequency of reciprocation thereof may be varied independently, allowing flexible adjustment of the operation of the brush to individual needs.

* * * * *